United States Patent [19]

Brooks et al.

[11] Patent Number: 5,668,146

[45] Date of Patent: Sep. 16, 1997

[54] SYMMETRICAL BIS-HETEROARYLMETHOXYPHENYLIMI-NOXYALKYL CARBOXYLATES AS INHIBITORS OF LEUKOTRIENE BIOSYNTHESIS

[75] Inventors: Clint D. W. Brooks; Pramila Bhatia, both of Libertyville; Teodozyj Kolasa, Lake Villa, all of Ill.

[73] Assignee: Abbott Laboratories, Abbott Park, Ill.

[21] Appl. No.: 703,442

[22] Filed: Sep. 17, 1996

Related U.S. Application Data

[60] Provisional application No. 60/004,822 Oct. 3, 1995.

[51] Int. Cl.$^6$ .......................... A61K 31/47; A61K 31/44; C07D 215/14; C07D 213/30
[52] U.S. Cl. .......................... 514/311; 514/357; 546/174; 546/335
[58] Field of Search ............................ 546/174, 335; 514/311, 357

[56] References Cited

U.S. PATENT DOCUMENTS

| | | | |
|---|---|---|---|
| 2,901,464 | 8/1959 | Schaefer | 260/67.6 |
| 3,862,982 | 1/1975 | Welstead | 260/482 C |
| 4,868,193 | 9/1989 | Lee | 514/314 |
| 4,970,215 | 11/1990 | Mohrs | 514/311 |
| 4,992,576 | 2/1991 | Gapinski | 560/52 |
| 5,358,955 | 10/1994 | Brooks | 514/311 |
| 5,399,699 | 3/1995 | Kolasa | 546/174 |
| 5,420,282 | 5/1995 | Brooks | 546/174 |
| 5,512,581 | 4/1996 | Brooks | 514/311 |

FOREIGN PATENT DOCUMENTS

| | | |
|---|---|---|
| A0349062 | 1/1990 | European Pat. Off. . |
| WO9414762 | 7/1994 | WIPO . |
| WO9602507 | 2/1996 | WIPO . |

OTHER PUBLICATIONS

Musser et al., J. Med. Chem 1992, 35, 2501–2524.
Prasit et al; Bioorganic and Medicinal Chemistry Letters 1(11) 645–648 (1991).

*Primary Examiner*—C. Warren Ivy
*Assistant Examiner*—Evelyn Huang
*Attorney, Agent, or Firm*—Monte R. Browder

[57] ABSTRACT

Compounds having the formula:

$$W-CH_2-O-Y-CH(O-N=A-C(=O)-M)-Y-O-CH_2-W$$

or a pharmaceutically acceptable salt thereof wherein W and Y at each occurrence are the same and W is selected from the group consisting of optionally substituted quinolyl, optionally substituted benzothiazolyl, optionally substituted benzoxazolyl, optionally substituted benzimidazolyl, optionally substituted quinoxalyl, optionally substituted pyridyl, optionally substituted pyrimidyl, and optionally substituted thiazolyl; Y is selected from optionally substituted phenylene and optionally substituted —⟨phenylene⟩—(alkylene)— wherein the alkylene portion is of one to six carbon atoms; A is selected from alkylene, alkenylene, cycloalkylene, and optionally substituted —(alkylene)—⟨phenylene⟩— wherein the alkylene portion is of one to six carbon atoms; and M is selected from hydrogen, a pharmaceutically acceptable cation, a pharmaceutically acceptable, metabolically cleavable group, —$OR^3$, and —$NR^4R^5$, inhibit leukotriene biosynthesis and are useful in the treatment of allergic and inflammatory disease states. Also disclosed are leukotriene biosynthesis inhibiting compositions and a method of inhibiting leukotriene biosynthesis in a mammal.

12 Claims, No Drawings

SYMMETRICAL BIS-HETEROARYLMETHOXYPHENYLIMI-NOXYALKYL CARBOXYLATES AS INHIBITORS OF LEUKOTRIENE BIOSYNTHESIS

CROSS REFERENCE TO RELATED APPLICATIONS

This application claims the benefit of U.S. Provisional Application No. 60/004,822, filed Oct. 3, 1995.

TECHNICAL FIELD

This invention relates to novel compounds which inhibit leukotriene biosynthesis, to pharmaceutical compositions comprising these compounds, and to a medical method of treatment. More particularly, this invention concerns symmetrical bis-heteroarylmethoxyphenylalkyl carboxylate compounds which inhibit leukotriene biosynthesis, to pharmaceutical compositions comprising these compounds and to a method of inhibiting leukotriene biosynthesis.

BACKGROUND OF THE INVENTION

The leukotrienes are extremely potent substances which produce a wide is variety of biological effects, often in the nanomolar to picomolar concentration range. Leukotrienes are important pathological mediators in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

Compounds which prevent leukotriene biosynthesis are thus useful in the treatment of disease states such as those listed above in which the leukotrienes play an important pathophysiological role.

U.S. Pat. No. 5,512,581 (Apr. 30, 1996) discloses iminoxycarboxylate derivatives which inhibit leukotriene biosynthesis. U.S. Pat. No. 5,399,699 (Mar. 21, 1995) discloses indole iminooxy derivatives which inhibit leukotriene biosynthesis.

U.S. Pat. No. 5,358,955 (Oct. 25, 1994) discloses aryl and heteroarylmethoxyphenyl compounds which inhibit leukotriene biosynthesis.

U.S. Pat. No. 4,970,215 (Nov. 13, 1990) discloses quinolylmethoxyphenyl acetic acid derivatives which inhibit leukotriene biosynthesis.

European Patent Application Number 349 062 (Jan. 3, 1990) discloses quinolylmethoxyphenyl alkanoic acid derivatives which inhibit leukotriene biosynthesis.

Prasit, et al., *Bioorganic and Medicinal Chemistry Letters*, 1 (11), 645 (1991) describe ((4-(4-chlorophenyl)-1-(4-(2-quinolylmethoxy)phenyl)butyl)thio)acetic acid as an orally active leukotriene biosynthesis inhibitor. Musser and Kraft, *J. Med. Chem.*, 35 (14), 1, (1992) review quinoline containing leukotriene biosynthesis inhibitors.

SUMMARY OF THE INVENTION

In its principal embodiment, the present invention provides certain symmetrical bis-heteroarylmethoxyphenylalkyl carboxylate compounds which inhibit leukotriene biosynthesis and are useful in the treatment of allergic and inflammatory disease states in which leukotrienes play a role.

The compounds of the present invention have the formula:

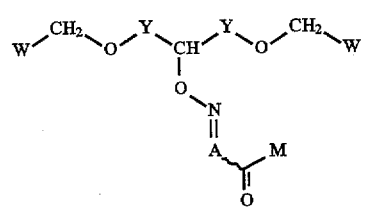

or a pharmaceutically acceptable salt thereof wherein W and Y, respectively, are the same at each occurrence.

The group W is selected from the group consisting of (a) quinolyl; (b) quinolyl substituted with a substituent selected from the group consisting of (b-1) halogen, (b-2) alkyl of one to six carbon atoms, (b-3) phenyl, (b-4) phenyl substituted with a substituent selected from the group consisting of (b-4-a) halogen, s (b-4b) alkyl of one to six carbon atoms, (b-4c) haloalkyl of one to six carbon atoms, and (b-4-d) alkoxy of one to six carbon atoms, (b-5) pyridyl, (b-6) pyridyl substituted with a substituent selected from the group consisting of (b-6-a) halogen, (iy6-b) alkyl of one to six carbon atoms, and (b-6-c) alkoxy of one to six carbon atoms; (c) benzothiazolyl; (d) benzothiazolyl substituted with a substituent selected from the group consisting of (d-1) halogen, (d-2) alkyl of one to six carbon atoms, (d-3) phenyl, (d-4) phenyl substituted with a substituent selected from the group consisting of (d-4-a) halogen, (d-4-b) alkyl of one to six carbon atoms, (d-4-c) haloalkyl of one to six carbon atoms, and (d-4-d) alkoxy of one to six carbon atoms, (d-5) pyridyl, and (d-6) pyridyl substituted with a substituent selected from the group consisting of (d-6-a) halogen, (d-6-b) alkyl of one to six carbon atoms, and (d-6-c) alkoxy of one to six carbon atoms; (e) benzoxazolyl; (f) benzoxazolyl substituted with a substituent selected from the group consisting of (f-1) halogen and (f-2) alkyl of one to six carbon atoms; (g) benzimidazolyl; (h) benzimidazolyl substituted with a substituent selected from the group consisting of (h-1) halogen, and (h-2) alkyl of one to six carbon atoms; (i) quinoxalyl; (j) quinoxalyl substituted with a substituent selected from the group consisting of (j-1) halogen and (j-2) alkyl of one to six carbon atoms; (k) pyridyl; (l) pyridyl substituted with a substituent selected from the group consisting of (l-1) phenyl, (l-2) phenyl substituted with a substituent selected from, the group consisting of (1-2-a) halogen, (1-2-b) alkyl of one to six carbon atoms, (1-2-c) haloalkyl of one to six carbon atoms, (1-2-d) alkoxy of one to six carbon atoms, (1-3) pyridyl, (1-4) pyridyl substituted with a substituent selected from the group consisting of (1-4-a) halogen, (1-4-b) alkyl of one to six carbon atoms, and (1-4-c) alkoxy of one to six carbon atoms; (m) pyrimidyl; (n) pyrimidyl substituted with a substituent selected from the group consisting of (n-1) phenyl, (n-2) phenyl substituted with a substituent selected from the group consisting of (n-2-a) halogen, (n-2-b) alkyl of one to six carbon atoms, (n-2-c) haloalkyl of one to six carbon atoms, and (n-2-d) alkoxy ol one to six carbon atoms, (n-3) pyridyl, (n-4) pyridyl substituted with a substituent selected from the group consisting of (n-4-a) halogen, (n-4-b) alkyl of one to six carbon atoms, and (n-4-c) alkoxy of one to six carbon atoms; (o) thiazolyl; (p) thiazolyl substituted with a substituent selected from the group consisting of (p-1) phenyl, (p-2) phenyl substituted with a substituent selected from the group consisting of (p-2-a) halogen, (p-2-b) alkyl of one to six carbon atoms, (p-2-c) haloalkyl of one to six carbon atoms, and (p-2-d) alkoxy of one to six carbon atoms, (p-3) pyridyl, and (p-4) pyridyl substituted with a substituent selected from the group consisting of (p-4-a) halogen, (p-4-b) alkyl of one to six carbon atoms, and (p-4-c) alkoxy of one to six carbon atoms.

The group Y is selected from the group consisting of (a) phenylene, (b) phenylene substituted with a substituent selected from the group consisting of (b-1) halogen, (b-2) alkyl of one to six carbon atoms, (b-3) haloalkyl of one to six carbon atoms, and (b-4) alkoxy of one to six carbon atoms,

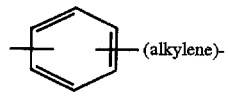 (c)

wherein the alkylene portion is of one to six carbon atoms, and

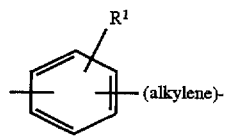 (d)

wherein the alkylene portion is of one to six carbon atoms, and $R^1$ is selected from the group consisting of (d-1) halogen, (d-2) alkyl of one to six carbon atoms, and (d-3) alkoxy of one to six carbon atoms.

The group A is selected from the group consisting of (a) alkylene of one to six carbon atoms, (b) alkenylene of two to six carbon atoms, (c) cycloalkylene of three to eight carbon atoms,

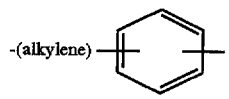 (d)

wherein the alkylene portion is of one to six carbon atoms, and

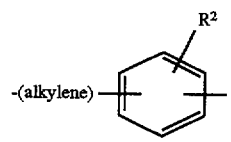 (e)

wherein the alkylene portion is of one to six carbon atoms, and $R^2$ is selected from the group consisting of (e-1) halogen, (e-2) alkyl of one to six carbon atoms, and (e-3) haloalkyl of one to six carbon atoms.

The group M is selected from the group consisting of (a) a pharmaceutically acceptable, (b) a metabolically cleavable group, (c) —$OR^3$ where $R^3$ is selected from hydrogen or alkyl of one to six carbon atoms, and (d) —$NR^4R^5$ where $R^4$ and $R^5$ are independently selected from the group consisting of (d-1) hydrogen, (d-2) alkyl of one to six carbon atoms, (d-3) hydroxy, and (d-4) alkoxy of one to six carbon atoms, or $R^4$ and $R^5$ taken together define a five- to eight-membered ring, with the proviso that $R^4$ and $R^5$ may not both be hydroxyl.

In those instances where M=OH, the compounds of the present invention are capable of forming base addition salts. In such instances, the term "pharmaceutically acceptable salts" refers to the relatively nontoxic inorganic and organic base addition salts of compounds of the present invention. These salts can be prepared in situ during the final isolation and purification of the compounds, or by separately reacting the purified carboxyl compound with a suitable base such as the hydroxide, carbonate, or bicarbonate of a pharmaceutically acceptable metal cation or with ammonia, or an organic primary, secondary, or tertiary amine of sufficient basicity to form a salt with the carboxyl functional group of the compounds of this invention.

Representative alkali or alkaline earth metal salts include sodium, lithium, potassium, calcium, magnesium, and the like. Representative organic amines useful for the formation of base addition salts include ethylamine, diethylamine, ethylene-diamine, ethanolamine, diethanolamine, piperazine, and the like. (See, for example, S. M. Berge, et al., *J. Pharmaceutical Sciences*, 1977, 66: 1–19, which is incorporated herein by reference).

Similarly, in those instances where the compounds of the present invention possess a heterocyclic ring moiety containing a basic nitrogen atom, the compounds are capable of forming acid addition salts. In such cases, the term "pharmaceutically acceptable salts" refers to the relatively nontoxic inorganic and organic acid addition salts of compounds of the present invention. These salts can be prepared in situ during the final isolation and purification of the compounds, or by separately reacting the purified compound in its free-base form with a suitable inorganic or organic acid and isolating the salt thus formed. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. (See, for example, S. M. Berge, et al., *J. Pharmaceutical Sciences*, 1977, 66: 1–19, which is incorporated herein by reference). Said pharmaceutically acceptable acid and base addition salts are also contemplated as falling within the scope of the present invention.

The present invention also provides pharmaceutical compositions which comprise a therapeutically effective amount of compound as described above in combination with a pharmaceutically acceptable carrier.

The invention further relates to a method of inhibiting leukotriene biosynthesis in a host mammal in need of such treatment comprising administering to a mammal in need of such treatment a therapeutically effective amount of a compound as defined above.

DETAILED DESCRIPTION

As used throughout this specification and the appended claims, the following terms have the meanings specified.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms "alkoxy" and "alkoxyl" denote an alkyl group, as defined above, attached to the parent molecular moiety through an oxygen atom. Representative alkoxy groups include methoxy, ethoxy, propoxy, butoxy, and the like.

The term "alkenyl" as used herein refers to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term "alkylene" denotes a divalent group derived from a straight or branched chain saturated hydrocarbon by the removal of two hydrogen atoms, for example —$CH_2$—, —$CH_2CH_2$—, —$CH(CH_3)CH_2$—and the like.

The term "alkylphenyl" refers to an alkylene group attached to the parent molecular moiety through a phenyl group. Representative alkylphenyl groups include methylphenyl, ethylphenyl, propylphenyl, and the like.

The term "alkenylene" denotes a divalent group derived from a straight or branched chain hydrocarbon containing at least one carbon-carbon double bond. Examples of alkenylene include —CH=CH—, —$CH_2$CH=CH—, —$C(CH_3)$=CH—, —$CH_2$CH=CH$CH_2$—, and the like.

The term "cycloalkyl" as used herein refers to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

The term "cycloalkylene" denotes a divalent radical derived from a cycloalkane by the removal of two hydrogen atoms.

The term "haloalkyl" denotes an alkyl group, as defined above, having one, two, or three halogen atoms attached thereto and is exemplified by such groups as chloromethyl, bromoethyl, trifluoromethyl, and the like.

As used throughout this specification and the appended claims, the term "metabolically clearable group" denotes a moiety which is readily cleaved in vivo from the compound bearing it, which compound after cleavage remains or becomes pharmacologically active. Metabolically cleavable groups form a class of groups reactive with the carboxyl group of the compounds of this invention (where M is —OH) well known to practitioners of the art. They include, but are not limited to such as groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds of this invention are cleaved in vivo, the compounds bearing such groups act as pro-drugs of other leukotriene biosynthesis inhibitors. The compounds bearing the metabolically cleavable groups have the advantage that they may exhibit improved bioavailability as a result of enhanced solubility and/or rate of absorption conferred upon the parent compound by virtue of the presence of the metabolically cleavable group.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products followed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

Preferred Embodiments

Examples of compounds contemplated as falling within the scope of the present invention include, but are not limited to:

bis(4-(2-quinolylmethoxy)phenyl)methyliminoxyacetic acid, 2-(bis(4-(2-quinolylmethoxy)phenyl)methyliminoxy) propionic acid, bis(4-(2-pyridylmethoxy)phenyl)methyliminoxyacetic acid, 2-(bis(4-(2-pyridylmethoxy)phenyl)methyliminoxy) propionic acid, bis(4-(6-fluoro-2-quinolylmethoxy)phenyl) methyliminoxyacetic acid, 2-(bis(4-(6-fluoro-2-quinolylmethoxy)phenyl) methyliminoxy)propionic acid, 4-(bis(4-(2-quinolylmethoxy)phenyl)methyliminoxy) pentanoic acid, 4-(bis(4-(2-quinolylmethoxyphenyl)methyliminoxy) pent-2-enoic acid, 3-(1,5-bis(4-(2-quinolylmethoxy)phenyl)pentyl) iminoxyacetic acid, 2-(3-(1,5-bis(4-(2-quinolylmethoxy)phenyl)pentyl) iminoxy)propionic acid, 2-(bis(4-(2-quinolylmethoxy)phenyl)methyliminoxy) propionic acid sodium salt, 4-(bis(4-(2-quinolylmethoxy)phenyl)methyliminoxy) pentanoic acid sodium salt, 2-(bis(4-(2-benzothiazolyllmethoxy)phenyl) methyliminoxy)propionic acid, 2-(bis(4-(2-benzoxazolylmethoxy)phenyl) methyliminoxy)propionic acid, 2-(bis(4-(1H-1-methyl-2-benzimidazolylmethoxy) phenyl)methyliminoxy)-propionic acid, 2-(bis(4-(2-quinoxalylmethoxy)phenyl)methyliminoxy) propionic acid, 2-(bis(4-(2-pyrimidylmethoxy)phenyl)methyliminoxy) propionic acid, 2-(bis(4-(4-phenyl-2-thiazolylmethoxy)phenyl) methyliminoxy)propionic acid, and 2-(bis(4-(4-(pyrid-2-yl)-2-thiazolylmethoxy)phenyl) methyliminoxy)propionic acid.

Preferred compounds of the present invention have the structure above wherein M=—OH or a pharmaceutically acceptable salt of the carboxylate anion of M=—OH.

More preferred compounds of the present invention have the structure immediately above wherein A is alkyl of one to six carbon atoms.

Still more preferred compounds of the present invention have the structure immediately above wherein W is quinolyl or benzothiazolyl. The most preferred compounds of the present invention have the structure immediately above wherein Y is phenyl and W is quinolyl.

Compounds representative of the most preferred embodiment include, but are not limited to bis(4-(2-quinolylmethoxy)phenyl)methylirninoxyacetic acid, 2-(bis(4-(2-quinolylmethoxy)phenyl)methyliminoxy) propionic acid, 4-(bis(4-(2-quinolylmethoxy)phenyl)methyliminoxy) pentanoic acid, 2-(bis(4-(2-quinolylmethoxy)phenyl)methyliminoxy) propanoic acid sodium salt, and 4-(bis(4-(2-quinolylmethoxy)phenyl)methyliminoxy) pentanoic acid sodium salt.

Lipoxygenase Inhibition Determination

Inhibition of leukotriene biosynthesis was evaluated in an assay involving calcium ionophore-induced $LTB_4$ expressed in human polymorphonuclear leukocytes (PMNL). Human PMNL isolated from heparinized (20 USP units/mL) venous blood (25 mL) obtained from healthy volunteers was layered over an equal volume of Ficoll-Hypaque Mono-Poly Resolving Medium (ICN Flow, Costa Mesa, Calif.) and centrifugated at 400×g for 40 minutes at 20° C. The PMNL was collected, erythrocytes lysed and washed 2× and suspended at $1.0 \times 10^7$ cells/mL in Earle's balanced salt solution with 17 mM Earle's HEPES. Aliquots of the cell suspension were preincubated with test compounds dissolved in DMSO (final concentration <2%) for 15 minutes and stimulated with calcium ionophore (final concentration 8.3 µM) for 10 minutes at 37° C. Incubations were stopped with the addition of two volumes of ice cold methanol followed by centrifuging the cell suspensions at 4° C. for 10 minutes at 450×g. The amount of $LTB_4$ in the methanol extract was analyzed by enzyme-linked immunoassay or by HPLC analysis.

The compounds of this invention inhibit leukotriene biosynthesis as shown by the data for representative examples in Table 1.

TABLE 1

In Vitro Inhibitory Potencies Against 5-Lipoxygenase From Stimulated $LTB_4$ Formation in Human Polymorphonuclear Leukocytes

| Example | $IC_{50}$ (µM) |
|---|---|
| 1 | 0.068 |
| 2 | 0.160 |
| 6 | 0.040 |
| 7 | 0.050 |
| 8 | 0.030 |

Inhibition of leukotriene biosynthesis in vivo was evaluated using the Ionophore A-23187-Induced Rat Plueral Inflammation Model. Pleural inflammation was induced in male rats following the method of Rao, et al. (Rao, T. S., Currie, J. L., Shaffer, A. F., Isakson, P. C., Evaluation of 5-lipoxygenase Inhibitors, Zileuton, A78773 and ICI D-2 138 in an Ionophore (A-23187) Induced Pleural Inflammation Model in the Rat, Life Sciences, 53, 147 (1993)). Rats were dosed with experimental compounds in 0.2% methocel one hour prior to the intrapleural injection of the calcium ionophore, A23187. The rats where lightly anaesthetized with Pentrane (Abbott Laboratories) and injected intrapleurally with 0.5 ml of 2% ethanol in injectable saline (Abbott Laboratories) containing 20 µg of A23187 (Cal BioChem-Novabiochem). Thirty minutes later the animals were euthanised and the pleural cavities lavaged with ice cold saline (Abbott Laboratories). The lavage fluid was then added to ice cold methanol (final methanol concentration 30%) to lyse cells and precipitate protein. Eicosanoids were determined by enzyme immunoassay by standard methods.

TABLE 2

In Vivo Leukotriene Inhibition in Rat Pleural Inflammation

| Example | $ED_{50}$ |
|---|---|
| 2 | 2 mg/kg |
| 7 | 1 mg/kg |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is deskable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drag form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, slucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients. Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33, et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient if desired, the effective daily dose may be divided into multiple doses for purposes of administration, e.g., two to four separate doses per day.

Preparation of Compounds of this Invention

The compounds of this invention can be prepared by the representative methods described as follows. A general procedure for the synthesis of iminoxyalkylcarboxylate derivatives of Formula (W—CH$_2$O—Y—)$_2$CH—O—N=COM is outlined in Scheme 1. Commercially available 4,4'-dihydroxybenzophenone I is reacted with the requisite heteroarylmethylhalide (W—CH$_2$X where X is Cl, Br, or I and W is defined above) in the presence of a suitable base such as K$_2$CO$_3$ to provide the bis adduct II. Reduction of II by known methods, for example using NaBH$_4$ provides the corresponding hydroxy intermediate III. The hydroxy intermediate III is converted by known methods, for example by Mitsunobu reaction with N-hydroxyphthalimide as nucleophile to provide IV which is converted to the corresponding hydroxylamine V by treatment with hydrazine hydrate. The hydroxylamine intermediate V is then reacted in a standard manner with the requisite carbonyl unit, O=CR—A—COM to provide the compounds of this invention represented by the general structure VI.

Scheme 1

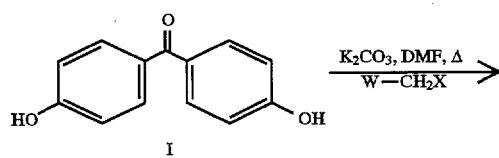

11

-continued
Scheme 1

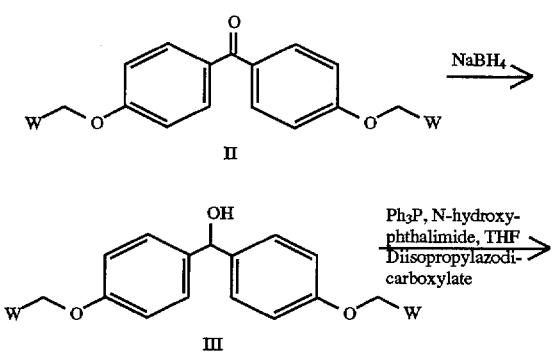

12

-continued
Scheme 1

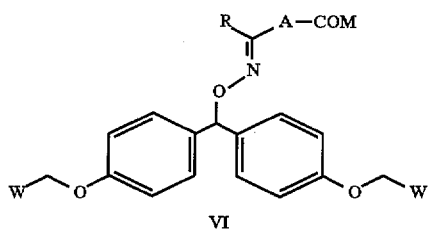

The foregoing may be better understood by reference to the following examples which are provided for illustration and not intended to limit the scope of the inventive concept The foregoing may be better understood by reference to the following examples which are provided for illustration and not intended to limit; the scope of the inventive concept.

EXAMPLE 1

Preparation of bis(4-(2-quinolylmethoxy)phenyl) methyliminoxyacetic acid

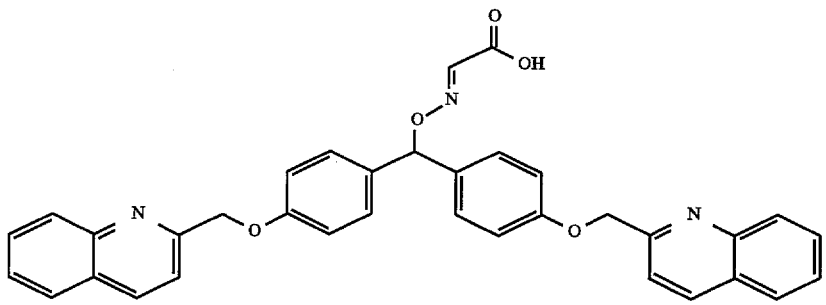

-continued
Scheme 1

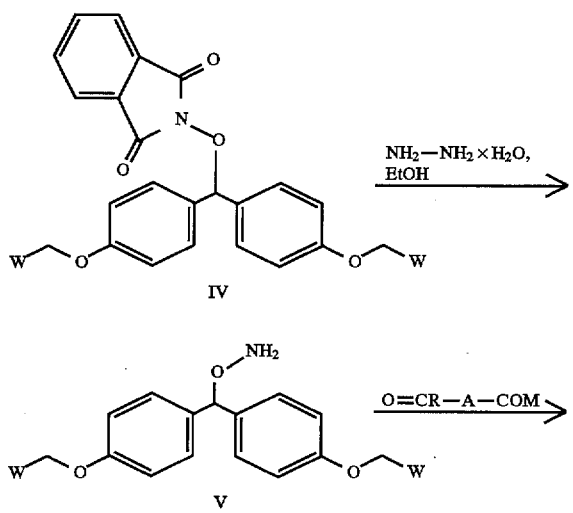

Step 1: bis(2-quinolylmethoxyphenyl) ketone

To a solution of 4-4'-dihydroxybenzophenone (4.22 g, 20 mmol) and $K_2CO_3$ (16.5 g, 120 mmol) in DMF (75 mL) was added 2-chloromethylquinoline hydrochloride (8.56 g, 40 mmol), and the resulting solution was stirred at 60° C. for 16 hours. The reaction mixture was then poured into ice water (100 mL). The resulting solid was filtered, slurried in 20% ether/hexane, filtered, and dried in vacuo to afford bis(2-quinolylmethoxyphenyl) ketone (9.3 g, 94%).

Step 2: bis(4-(2-quinolylmethoxy)phenyl)methanol

To a solution of bis(4(2-quinolylmethoxy)phenyl ketone (1.25 g, 2.5 mmol), prepared as in step 1, in $THF/CH_3OH$ (1:1, 60 mL) at room temperature was added $NaBH_4$ (0.37 g, 10 mmol) and the mixture was refluxed for 3 hours, concentrated in vacuo, suspended in water and neutralized with citric acid. The resulting precipitate was collected by filtration, washed with 20% $Et_2O$/hexane and dried in vacuo to afford bis(4-(2-quinolylmethoxy)phenyl)methanol (1.1 g, 88%) as white solid.

N-phthaloyl-O-[bis(4-(2-quinolylmethoxy)phenyl)methyl] hydroxylamine

To a mixture in THF (60 mL) of bis(4-(2-quinolylmethoxy)phenyl)methanol (1.1 g, 2.2 mmol), prepared as in step 2, triphenylphosphine (0.65 g, 2.5 mmol) and N-hydroxyphthalimide (0.41 g, 2.5 mmol) was added dropwise a solution of diisopropylazodicarboxylate (0.5 mL, 2.5 mmol) in THF (15 mL). The mixture was stirred at ambient temperature for 14 hours and concentrated in vacuo. Purification of the residue by chromatography on silica gel (9:1 CH$_2$Cl$_2$/EtOAC) provided N-phthaloyl-O-[bis(4-(2-quinolylmethoxy)phenyl)methyl]hydroxylamine (2.2 g) as an oil.

Step 4: O-bis(4-(2-quinolylmethoxy)phenyl) methylhydroxylamine

A solution in ethanol (80 mL) of N-phthaloyl-O-[bis(4-(2-quinolylmethoxy)phenyl)methyl]hydroxylamine (2.2 g, 2.1 mmol), prepared as in step 4, and hydrazine hydrate (1.5 mL, 30 mmol) was refluxed for 30 minutes and then cooled to room temperature. The reaction mixture was concentrated, 10% aqueous Na$_2$CO$_3$ (50 mL) was added and the mixture was extracted with CH$_2$C$_2$ (120 mL). The extract was washed with water (2×50 mL) and brine, dried over MgSO$_4$, filtered and concentrated in vacuo to provide O-bis(4-(2-quinolylmethoxy)phenyl)methylhydroxylamine (1.1 g).

Step 5: bis(4-2-quinolylmethoxy)phenyl) methyliminoxyacetic acid,

A mixture of O-bis(4-(2-quinolylmethoxy)phenyl) methylhydroxylamine (513 mg, 1.0 mmol), prepared as in step 4, glyoxylic acid hydrate (180 mg, 2.0 mmol), acetic acid (0.06 mL, 1.0 mmol) in CH$_3$OH (40 mL), THF (60 mL) and water (20 mL) was stirred at room temperature for 16 hours. The reaction mixture was then concentrated in vacuo and the precipitated solid was collected by filtration and recrystallized from ethyl acetate-hexane to afford bis(4-(2-quinolylmethoxy)phenyl)-methyliminoxyacetic acid (425 mg, 64%). mp 173° C. 1H NMR (300 MHz, DMSO-d6) δ 5.38 (s, 4H), 6.30 (s, 1H), 7.05 (d, 4H, J=8 Hz), 7.28 (d, 4H, J=8 Hz), 7.65 (m, 5H), 7.79 (m, 2H), 8.01 (t, 4H, J=8 Hz), 8.41 (d, 2H, J=8 Hz), 13.30 (bs, 1H). MS (DCI/NH$_3$) m/e 570 (M+H)$^+$. Anal. Calc'd. for C$_{35}$H$_{27}$N$_3$O$_5$: C, 72.66; H,4.84; N, 7.27. Found: C, 72.75; H, 4.99; N,7.06.

EXAMPLE 2

Preparation of 2-(bis(4-(2-quinolylmethoxy)phenyl) metheyliminoxy)propionic acid

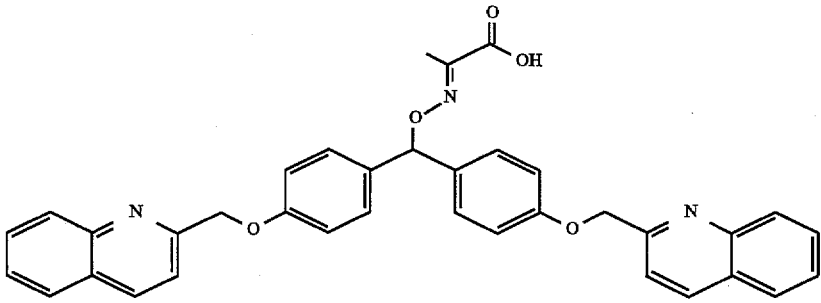

Step 1: 2-(bis(4-(2-quinolylmethoxy)phenyl)-methyliminoxy)propic acid methyl ester A mixture of O-bis(4-(2-quinolylmethoxy)phenyl) methylhydroxylamine (513 mg, 1.0 mmol), prepared as in Example 1, step 4, methyl pyruvate (0.14 mL, 1.5 mmol) and acetic acid (0.06 mL, 1.0 mmol) in CH$_3$OH (40 mL), THF (60 mL) and water (20 mL) was stirred at room temperature for 24 hours and then was concentrated in vacuo. Water (25 mL) was added to the residue and the mixture was extracted with CH$_2$Cl$_2$, dried over MgSO$_4$, filtered and concentrated in vacuo. The residue was chromatographed (silica gel, 3:1 hexane-ethyl acetate) to afford 2-(bis(4-(2-quinolylmethoxy)phenyl)methyliminoxy) propionic acid methyl ester (410 mg) as an oil.

Step 2: 2-(4-(2-quinolylmethoxy)phenyl)methyliminoxy) propionic acid

To a solution of the 2-(bis(4-(2-quinolylmethoxy)phenyl) methyliminoxy)propic acid methyl ester prepared in step 1 in CH$_3$OH (75 mL) was added aqueous 1N NaOH (5 mL) and the mixture was stirred at room temperature for 16 hours and then was concentrated in vacuo. The residue was dissolved in water (25 mL) and the aqueous solution was washed with ethyl ether (25 mL) and then acidified with 50% aqueous citric acid. The precipitated solid was collected by filtration, dried in vacuo and recrystallized from ethyl acetate-hexane to provide 2-(bis(4-(2-quinolylmethoxy)phenyl)methyliminoxy)propionic acid as a mixture of E and Z isomers (245 mg). mp 94°–96° C. $^1$H NMR (300 MHz, DMSO-d$_6$) δ 2.03 (s, 3H), 5.35 (s, 4H), 6.27 (s, 1H), 7.04 (d, 4H, J=8 Hz), 7.25 (d, 4H, J=8 Hz), 7.63 (m, 4H), 7.78 (t, 2H, J=8 Hz), 8.02 (t, 4H, J=8 Hz), 8.41 (d, 2H, J=9 Hz). MS (FAB$^+$) m/e: 584 (M+H)$^+$. Anal. Calc'd. for C$_{36}$H$_{29}$N$_3$O$_5$×H$_2$O: C, 71.94; H, 5.16; N, 6.99. Found: C, 72.44; H, 5.15; N, 6.78.

EXAMPLE 3

Preparation of bis(4-(2-pyridylmethoxy)phenyl) methyliminoxyacetic acid

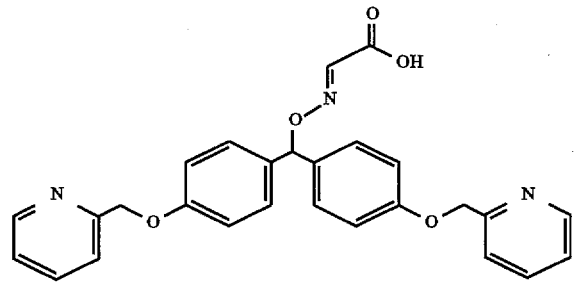

The desired compound was prepared according to the procedure of Example 1, except substituting 2-chloromethylpyridine for 2-chloromethylquinoline. mp 153° C. $^1$H NMR (300 MHz, DMSO-d$_6$) d 5.18 (s, 4H), 6.31 (s, 1H), 7.01 (d, 4H, J=9 Hz), 7.26 (d, 4H, J=9 Hz), 7.33 (m, 2H), 7.26 (d, 4H, J=9 Hz), 7.33 (m, 2H), 7.50 (d, 2H, J=9 Hz), 7.71 (s, 1H), 7.83 (m, 2H), 8.57 (m, 2H). MS (FAB$^+$) m/e: 468 (M-H)$^+$. Anal. Calc'd. for C$_{27}$H$_{23}$N$_3$O$_5$×H$_2$O: C, 67.78; H, 5.02; N, 8.80. Found: C, 67.94; H, 4.85; N, 8.69.

EXAMPLE 4

Preparation of 2-(bis(4-(2-pyridylmethoxy)phenyl)methyliminoxy)propionic acid

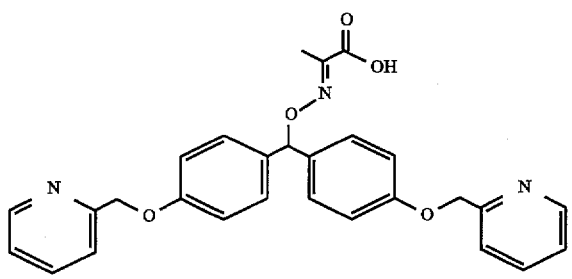

The desired compound was prepared according to the procedure of Example 2, except substituting 2-chloromethylpyridine for 2-chloromethylquinoline. mp 174° C. $^1$H NMR (300 MHz, DMSO-d$_6$) d 2.04 (s, 3H), 5.15 (s, 4H), 6.39 (s, 1H), 7.0 (d, 4H, J=9 Hz), 7.25 (d, 4H, J=9 Hz), 7.34 (m, 2H), 7.26 (d, 4H, J=9 Hz), 7.33 (m, 2H), 7.51(d, 2H, J=9 Hz), 7.73 (m, 2H), 8.57 (m, 2H). MS (FAB$^+$) m/e: 399, 381 (M-102; ON=C(CH$_3$)CO$_2$H). Anal. Calc'd. for C$_{28}$H$_{25}$N$_3$O$_5$×H$_2$O: C, 67.12; H, 5.39; N, 8.39. Found: C, 67.57; H, 5.33; N, 8.23.

EXAMPLE 5

Preparation of bis(4-(6-fluoro-2-quinolylmethoxy)phenyl)methyliminoxyacetic acid

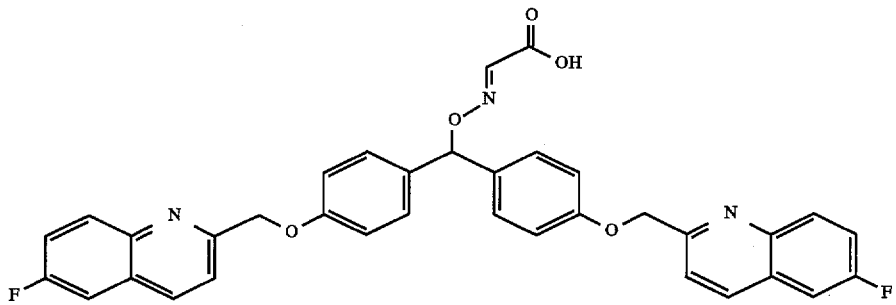

The desired compound was prepared according to the procedure of Example 1, except substituting 2-bromomethyl-6-fluoroquinoline for 2-chloromethylquinoline. mp 149° C. $^1$H NMR (300 MHz, DMSO-d$_6$) d 5.34 (s, 4H), 6.31 (s, 1H), 7.05 (d, 4H, J=9 Hz), 7.28 (d, 4H, J=9 Hz), 7.61 (m, 5H), 7.81 (m, 2H), 8.08 (m, 2H), 8.41 (d, 2H, J=9 Hz). MS (DCI/NH$_3$) m/e: 606 (M+H)$^+$. Anal. Calc'd. for C$_{35}$H$_{25}$F$_2$N$_3$O$_5$×2H$_2$O: C, 65.68; H, 4.52; N, 6.55. Found: C, 66.0; H, 4.35; N, 6.38.

EXAMPLE 6

Preparation of 2-(bis(4-(6-fluoro-2-quinolylmethoxy)phenyl)methyliminoxy)propionic acid

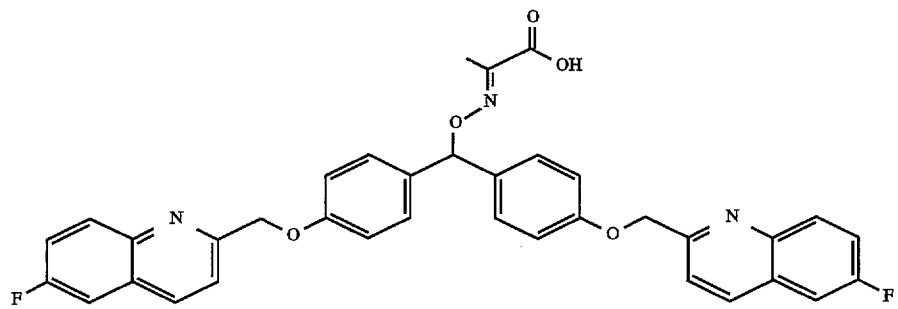

The desired compound was prepared according to the procedure of Example 2, except substituting 2-bromomethyl-6-fluoroquinoline for 2-chloromethylquinoline. mp 145° C. 1H NMR (300 MHz, DMSO-$d_6$) d 2.03 (s, 3H), 5.33 (s, 4H), 6.30 (s, 1H), 7.04 (d, 4H, J=9 Hz), 7.28 (d, 4H, J=9 Hz), 7.71 (m, 4H), 7.81 (dd, 2H, J=9, 3 Hz), 7.81 (dd, 2H, J=9, 3 Hz). MS (DCI/NH$_3$) m/e: 517 (M-102; ON=C(CH$_3$)CO$_2$H). Anal. Calc'd. for $C_{36}H_{27}F_2N_3O_5 \times 2H_2O$: C, 66.03; H, 4.44; N, 6.25. Found: C, 65.95; H, 4.53; N, 6.42.

EXAMPLE 7

Preparation of 4-bis(4-(2-quinolylmethoxy)phenyl)methyliminoxy entanoic acid

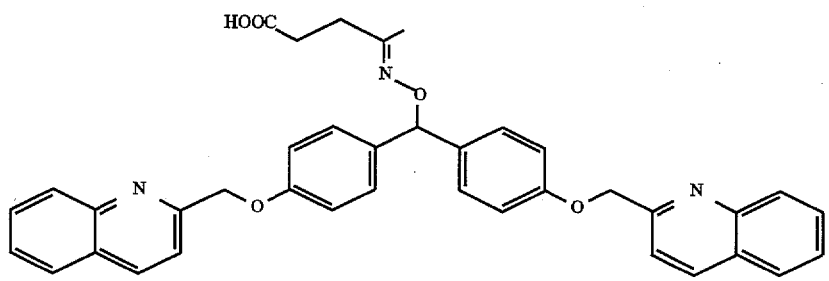

Step 1: 4-(bis(4-(2-quinolylmethoxy)phenyl)methyliminoxy) pentanoic acid ethyl ester A mixture of O-bis(4-(2-quinolylmethoxy)phenyl)methylhydroxylamine (410 mg, 0.8 mmol), prepared as in Example 1, steps 1–4, ethyl levulinate (0.11 mL, 0.8 mmol) and acetic acid (0.05 mL, 0.8 mmol) in dioxane (20 mL) and methanol (10 mL) was stirred at room temperature for 12 hours and then concentrated in vacuo. The residue was dissolved in ethyl acetate (50 mL) and the organic solution was washed with water, 10% sodium bicarbonate, water, and brine, dried over MgSO$_4$, filtered, and concentrated in vacuo. Chromatography on silica gel (methylene chloride-ethyl acetate 4:1) provided 4-(bis(4-(2-quinolylmethoxy)phenyl)methyliminoxy)pentanoic acid ethyl ester (580 mg).

Step 2: 4-(bis(4-(2-quinolylmethoxy)phenyl)methyliminoxy)pentanoic acid

To a solution of 4-(bis(4-(2-quinolylmethoxy)phenyl)methyliminoxy)pentanoic acid ethyl ester (580 mg), prepared as in step 1, in dioxane (15 mL) and ethanol (10 mL) was added aqueous 1N NaOH (1 mL, 1 mmol), and the resulting mixture was stirred at room temperature for 10 hours, concentrated in vacuo and diluted with water (50 mL). The resulting solution was acidified to pH 3 with 10% citric acid, the precipitated solid was filtered, washed with water, and dried in vacuo to provide 4-(bis(4-(2-quinolylmethoxy)phenyl)methyliminoxy)pentanoic acid (465 mg). mp 76°–78° C. (after crystallization from ethyl acetate-hexane). $^1$H NMR (300 MHz, DMSO-$d_6$) d 1.75 and 1.88 (two s, 1:4, 3H), 2.35 and 2.57 (s+m, 4:1, 4H), 5.33 (s, 4H), 6.03 (two s, 1:4, 1H), 7.00 (d, 4H, J=8 Hz), 7.22 (d, 4H, J=8 Hz), 7.64 (m, 4H), 7.80 (m, 2H), 8.00 (m, 4H), 8.40 (d, 2H, J=9 Hz). MS (DCI/NH$_3$) m/e: 612 (M+H)$^+$. Anal. Calc'd. for $C_{38}H_{33}N_3O_5$: C, 74.62; H, 5.44; N, 6.87. Found: C, 74.42; H, 5.37; N, 6.63.

EXAMPLE 8

Preparation of 4-(bis(4-(2-quinolylmethoxyphenyl)methyliminoxy)pent-2-enoic acid

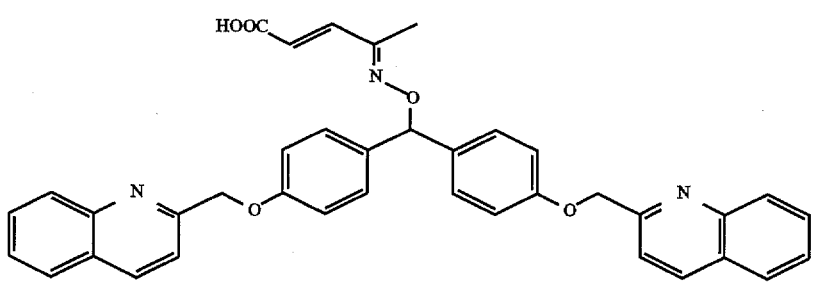

A mixture of O-bis(4-(2-quinolylmethoxy)phenyl)methylhydroxylamine (410 mg, 0.8 mmol) prepared as in Example 1, steps 1–4, 4-oxo-2-pentenoic acid (92 mg, 0.8 mmol) and acetic acid (0.05 mL, 0.8 mmol) in dioxane (20 mL) and methanol (10 mL) was stirred at room temperature for 14 hours and then concentrated in vacuo. The residue was dissolved in ethyl acetate (50 mL) and the resulting solution was washed with water and brine, dried over MgSO$_4$, filtered, and concentrated in vacuo. The residue was crystallized from methylene chloride-hexane to afford 4-(bis(4-(2-quinolylmethoxyphenyl)methyliminoxy)pent-2-enoic acid (420 mg). mp 93°–94° C. $^1$H NMR (300 MHz, DMSO-$d_6$) d 1.95 and 2.06 (two s, 1:2, 3H), 5.37 (s, 4H), 6.23 (m, 2H), 7.05 (m, 4H), 7.24 (t, 4H, J=8 Hz), 7.62 (m, 4H), 7.78 (m, 2H) 8.00 (m, 4H), 8.40 (d, 2H, J=9 Hz). MS (DCI/NH$_3$)

m/e: 610 (M+H)⁺. Anal. Calc'd. for $C_{38}H_{31}N_3O_5 \times H_2O$: C, 72.71; H, 5.30; N, 6.69. Found: C, 73.24; H, 5.34; N, 6.42.

EXAMPLE 9

Preparation of 3-(1,5-bis(4-(2-quinolylmethoxy)phenyl)pentyl)iminoxyacetic acid

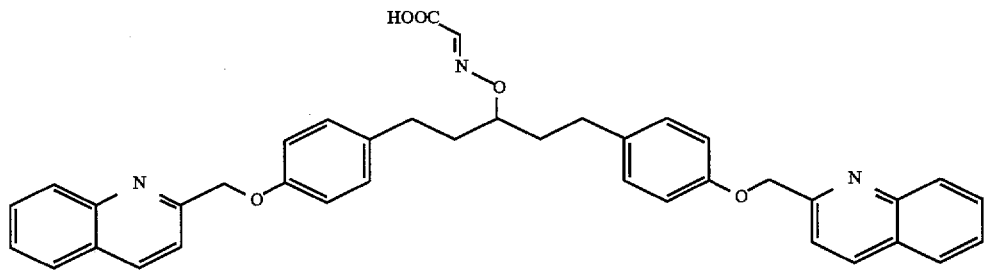

Step 1: 1,5-bis-(4-methoxyphenyl)-3-pentanone

To a solution of commercially available di(4-methoxybenzylidene) acetone (3.5 g, 12 mmol) in THF-MeOH (1:1,100 mL) was added platinum (IV) oxide (90 mg) and the resulting mixture was stirred at room temperature under 4 atmospheres of hydrogen for 19 hours. The catalyst was filtered and washed with THF, and the filtrate was concentrated in vacuo. The residue was purified by chromatography on silica gel (hexane-ethyl acetate 3:1) to provide 1,5-bis(4-methoxyphenyl)-3-pentanone (2.13 g) and the reduced side product 1,5-bis(4-methoxyphenyl)-3-pentanol (1.0 g).

Step 2: 1,5-bis(4-hydroxyphenyl)-3-pentanone

A mixture of 1,5-bis(4-methoxyphenyl)-3-pentanone (2.1 g, 7 mmol), prepared as in step 1, and aluminum tribromide (10.64 g, 40 mmol) in toluene (60 mL) was refluxed at 80° C. for 30 minutes and then cooled to room temperature. The reaction mixture was slowly added to a mixture of aqueous 1N HCl (150 mL) and ethyl ether (150 mL). The ether layer was separated, washed with aqueous 1N HCl, water, and brine, dried over MgSO₄, filtered, and concentrated in vacuo to provide 1,5-bis-(4-hydroxyphenyl)-3-pentanone (2 g).

Step 3: 1,5-bis(4-(2-quinolylmethoxy)phenyl)-3-pentanone

A solution of 1,5-bis(4-hydroxyphenyl)-3-pentanone (2.0 g, 8 mmol), prepared as in step 2, and potassium carbonate (2.76 g, 20 mmol) in DMF (40 mL) was treated with chloromethylquinoline (3.55 g, 20 mmol) at room temperature for 36 hours. The mixture was then poured into ice water (200 mL), and the precipitated solid was filtered, washed with water and dried in vacuo to afford crude 1,5-bis(4-(2-quinolylmethoxy)phenyl)-3-pentanone (5 g) which was used without further purification.

Step 4: 1,5-bis(4-(2-quinolylmethoxy)phenyl)-3-pentanol

To a solution of 1,5-bis(4-(2-quinolylmethoxy)phenyl)-3-pentanone (2.21 g, 4 mmol), prepared as in step 3, in dioxane (15 mL) and ethanol (35 mL) was added NaBH₄ (152 mg, 4 mmol) and the resulting mixture was refluxed for 30 minutes. The solution was then cooled to room temperature, acidified to pH 5 with 10% citric acid and concentrated in vacuo. To the residue was added water (50 mL) and the precipitated solid was filtered to afford 1,5-bis(4-(2-quinolylmethoxy)phenyl)-3-pentanol (2.3 g).

Step 5: N-phthaloyl-O-(1,5-bis(4-(2-quinolylmethoxy)phenyl)hydroxylamine

To a solution of 1,5-bis(4-quinolylmethoxy)phenyl-3-pentanol (2.3 g, 4 mmol), prepared as in step 4, N-hydroxyphthalimide (652 mg, 4 mmol) and triphenylphosphine (2.62 g, 10 mmol) in THF (45 mL) was added dropwise a solution of diisopropylazodicarboxylate (2 mL, 10 mmol) in THF (5 mL), and the resulting mixture was stirred at room temperature for 12 hours. The mixture was then concentrated in vacuo and the residue was purified by chromatography on silica gel (methylene chloride-ethyl acetate 12:1) to provide crude N-phthaloyl-O-(1,5-bis(4-(2-quinolylmethoxy)phenyl)-3-pentyl)hydroxylamine (4 g) used directly in the next step.

Step 6: O-(1,5-bis(4-(2-quinolylmethoxy)phenyl-3-pentyl)hydroxylamine

A mixture of the crude N-phthaloylhydroxylamine intermediate (4 g) and hydrazine hydrate (0.5 mL; 8 mmol) in dioxane (25 mL) and ethanol (25 mL) was 30 refluxed for 30 minutes The mixture was then treated with 10% Na₂CO₃ and extracted with ethyl acetate (150 mL). The organic extract was washed with water and brine, dried over MgSO₄, filtered and concentrated in vacuo. The residue was purified by chromatography on silica gel (ethyl acetate) to provide O-(1,5-bis(4-(2-quinolylmethoxy)phenyl)-3-pentyl)hydroxylamine (1.2 g).

Step 7: 3-(1,5-bis(4-(2-quinolylmethoxy)phenyl)pentyl)iminoxyacetic acid

A solution of hydroxylamine derivative (0.34 g, 0.6 mmol), glyoxylic acid hydrate (0.056 g, 0.6 mmol) and acetic acid (0.035 mL; 0.6 mmol) in dioxane (15 mL), methanol (10 mL) and water (5 mL) was stirred at room temperature for 12 hours. The mixture was then concentrated in vacuo, and the residue dissolved in ethyl acetate, washed with water and brine, dried over MgSO₄, filtered, and concentrated in vacuo to provide 3-(1,5-bis(4-(2-quinolylmethoxy)phenyl)-pentyl)iminoxyacetic acid. ¹H NMR (300 MHz, DMSO-d₆) d 1.85 (m, 4H), 2.55 (m, 4H), 4.16 (m, 1H), 5.33 (s, 4H), 6.94 (d, 4H, J=9 Hz), 7.10 (d, 4H, J=9 Hz), 7.62 (m+s, 5H), 7.78 (m, 2H), 8.00 (m, 4H), 8.40 (d, 2H, J=8 Hz). MS (DCI/NH₃) m/e: 626 (M+H)⁺. Anal. Calc'd. for $C_{39}H_{35}N_3O_5 \times H_2O$: C, 72.77; H, 5.79; N, 6.53. Found: C, 73.21; H, 5.71; N, 6.41.

EXAMPLE 10

Preparation of 2-(3-(1,5-bis(4-(2-quinolylmethoxy)phenyl)pentyl)iminoxy) propionic acid

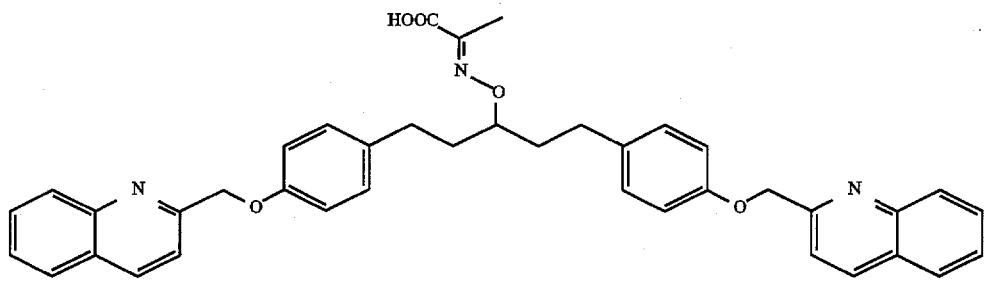

Step 1: 2-(3-(1,5-bis(4-(2-quinolylmethoxy)phenyl)pentyl)iminoxy) propionic acid methyl ester A mixture of O-(1,5-bis(4-(2-quinolylmethoxy)phenyl)-3-pentyl)hydroxylamone, prepared as in Example 9, steps 1–6, (342 mg, 0.6 mmol), methyl pyruvate (0.06 mL, 0.6 mmol) and acetic acid (0.035 mL, 0.6 mmol) in dioxane (20 mL) and methanol (10 mL) was stirred at room temperature for 16 hours. The mixture was concentrated in vacuo and the residue was dissolved in ethyl acetate, washed with water, 10% NaHCO$_3$ and brine, dried over MgSO$_4$, filtered, and concentrated in vacuo. The residue was purified by chromatography on silica gel (4:1 CH$_2$Cl$_2$, ethyl acetate) to afford 2-(3-(1,5-bis(4-(2-quinolylmethoxy)phenyl)pentyl)iminoxy) propionic acid methyl ester (400 mg).

Step 2: 2-(3-(1,5-bis(4-(2-quinolylmethoxy)phenyl)pentyl)iminoxy) propionic acid To a solution of the 2-(3-(1,5-bis(4-(2-quinolylmethoxy)phenyl)pentyl)iminoxy) propionic acid methyl ester prepared in step 1 in dioxane (15 mL) and methanol (10 mL) was added 1N NaOH (1 mL) and the resulting mixture was stirred at room temperature for 10 hours. The mixture was concentrated in vacuo, diluted with water (30 mL) and acidified to pH 3 with dilute HCl to afford 2-(3-(1,5-bis(4-(2-quinolylmethoxy)phenyl)pentyl)iminoxy) propionic acid (310 mg, 80%). mp 53°–55° C. (methylene chloride-hexane). $^1$H NMR (300 MHz, DMSO-d$_6$) d 1.90 (m+s, 7H), 2.55 (m, 4H), 4.18 (m, 1H), 5.33 (s, 4H), 6.96 (d, 4H, J=9 Hz), 7.09 4H, J=9 Hz), 7.64 (m, 4H), 7.78 (m, 2H), 8.00 (m, 4H), 8.40 (d, 2H, J=8 Hz); MS (DCI/NH$_3$) m/e: 640 (M+H)$^+$. Anal. Calc'd. for C$_{40}$H$_{37}$N$_3$O$_5$×0.5 H$_2$O: C, 74.06; H, 5.90; N, 6.48. Found: C, 74.49; H, 5.94; N, 6.32.

EXAMPLE 11

Preparation of 2-(bis(4-(2-quinolylmethoxy)phenyl)methyliminoxy)propionic acid sodium salt

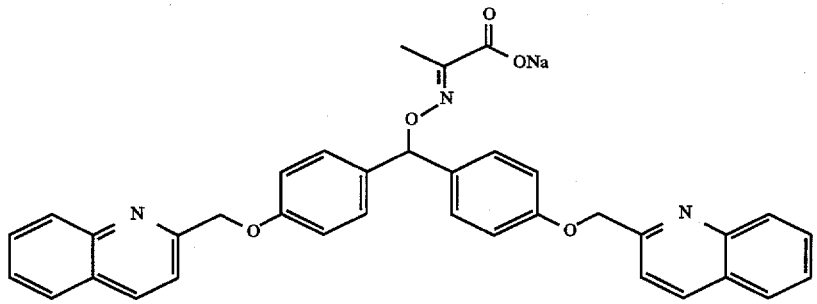

The desired product is prepared by treatment of 2-(bis(4-(2-quinolylmethoxy)-phenyl)methyliminoxy)propionic acid, prepared as in Example 2, with one equivalent of aqueous NaOH followed by drying in the usual manner.

EXAMPLE 12

Preparation of 4-(bis(4-(2-quinolylmethoxy)-phenyl)methyliminoxy)pentanoic acid sodium salt

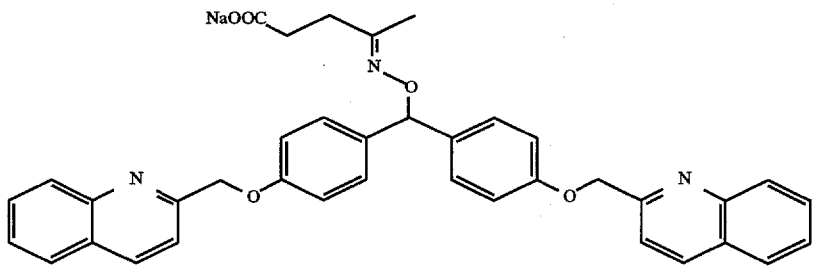

The desired product is prepared by treatment of 4-(bis(4-(2-quinolyl-methoxy)phenyl)methyliminoxy)pentanoic acid, prepared as in Example 7, with one equivalent of aqueous NaOH followed by drying in the usual manner.

The following additional examples are prepared according to the method described in Example 2, except substituting the requisite heteroarylmethylhalide W—$CH_2X$ where X is Cl, Br, or I for 2-chloromethylquinoline hydrochloride.

EXAMPLE 13

2-(bis(4-(2-benzothiazolylmethoxy)phenyl)methyliminoxy)propionic acid

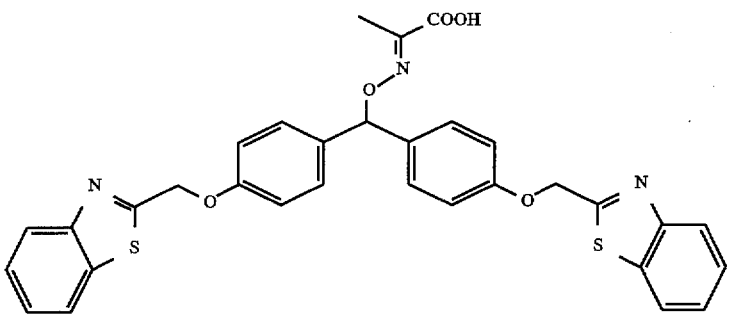

EXAMPLE 14

2-(bis(4-(2-benzoxazolylmethoxy)phenyl)methyliminoxy)propionic acid

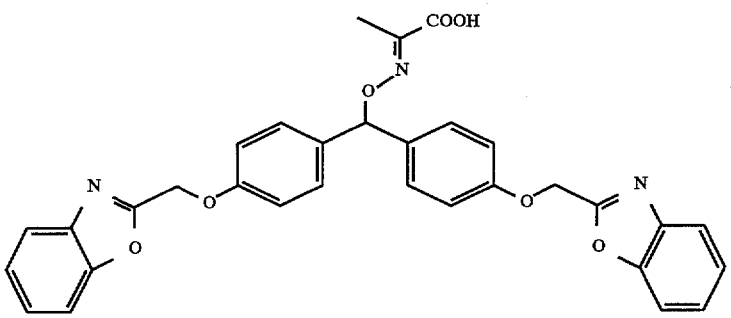

EXAMPLE 15

2-(bis(4-(1H-1-methyl-2-benzimidazolylmethoxy)-phenyl)methyliminoxy)propionic acid

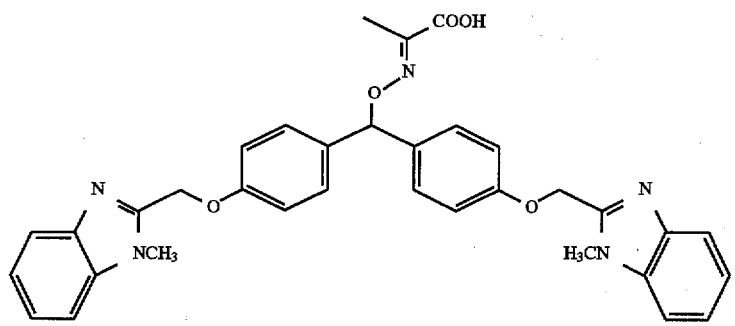
EXAMPLE 16
2-(bis(4-(2-quinoxalylmethoxy)phenyl)
methyliminoxy)propionic acid
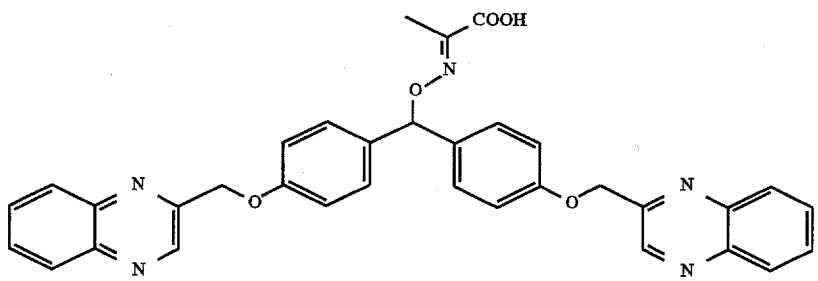
EXAMPLE 17
2-(bis(4-(2-pyrimidylmethoxy)phenyl)
methyliminoxy)propionic acid
EXAMPLE 18
2-(bis(4-(4-phenyl-2-thiazolylmethoxy)phenyl)
methyliminoxy)propionic acid
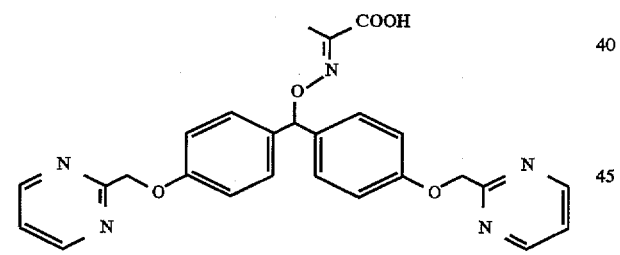
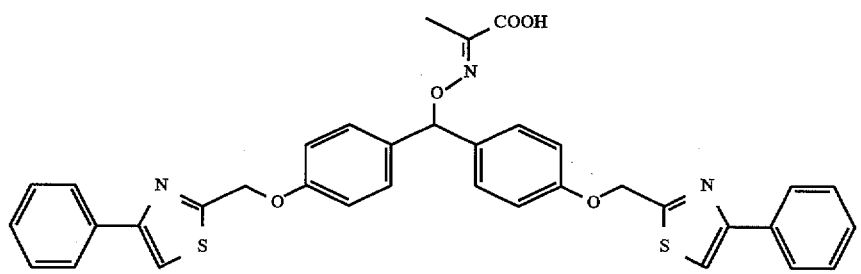

EXAMPLE 19

2-(bis(4-(4-(pyrid-2-yl)-2thiazolylmethoxy)phenyl)methyliminoxy)propionic acid

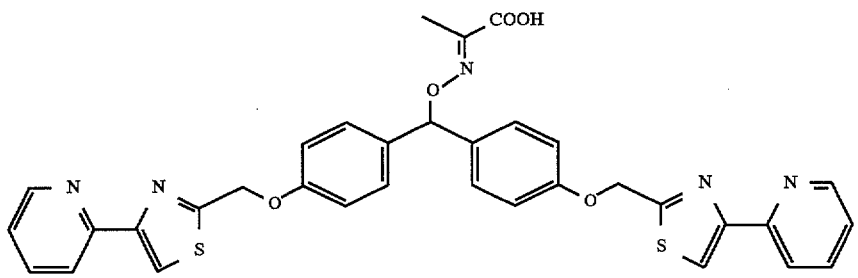

What is claimed is:

1. A compound having the formula:

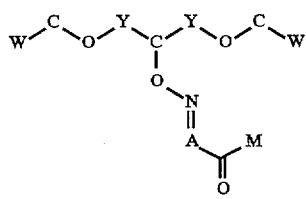

or a pharmaceutically acceptable salt or a metabolically cleavable group thereof wherein W and Y, respectively, are the same at each occurence; and W is selected from the group consisting of
- (a) quinolyl;
- (b) quinolyl substituted with a substituent selected from the group consisting of
  halogen,
  alkyl of one to six carbon atoms,
  phenyl,
  phenyl substituted with a substituent selected from the group consisting of
    halogen,
    alkyl of one to six carbon atoms,
    haloalkyl of one to six carbon atoms, and
    alkoxy of one to six carbon atoms,
  pyridyl,
  pyridyl substituted with a substituent selected from the group consisting of
    halogen,
    alkyl of one to six carbon atoms, and
    alkoxy of one to six carbon atoms;
- (c) pyridyl;
- (d) pyridyl substituted with a substituent selected from the group consisting of
  phenyl,
  phenyl substituted with a substituent selected from the group consisting of
    halogen,
    alkyl of one to six carbon atoms,
    haloalkyl of one to six carbon atoms, and
    alkoxy of one to six carbon atoms,
  pyridyl,
  pyridyl substituted with a substituent selected from the group consisting of
    halogen,
    alkyl of one to six carbon atoms, and
    alkoxy of one to six carbon atoms;

Y is selected from the group consisting of
- (a) phenylene,
- (b) phenylene substituted with a substituent selected from the group consisting of
  halogen,
  alkyl of one to six carbon atoms,
  haloalkyl of one to six carbon atoms, and
  alkoxy of one to six carbon atoms,

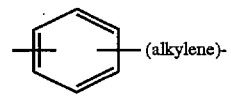 (c)

wherein the alkylene portion is of one to six carbon atoms, and

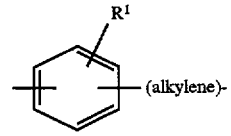 (d)

wherein the alkylene portion is of one to six carbon atoms, and $R^1$ is selected from the group consisting of
halogen,
alkyl of one to six carbon atoms, and
alkoxy of one to six carbon atoms;

A is selected from the group consisting of
- (a) alkylene of one to six carbon atoms,
- (b) alkenylene of two to six carbon atoms,
- (c) cycloalkylene of three to eight carbon atoms,

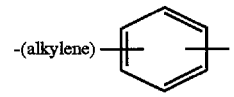 (d)

wherein the alkylene portion is of one to six carbon atoms, and

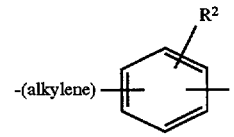 (e)

wherein the alkylene portion is of one to six carbon atoms, and $R^2$ is selected from the group consisting of
halogen, alkyl of one to six carbon atoms, and
haloalkyl of one to six carbon atoms;

M is selected from the group consisting of
—$OR^3$ where $R^3$ is selected from the group consisting of hydrogen, alkyl of one to six carbon atoms, and
—$NKR^4R^5$ where $R^4$ and $R^5$ are independently selected from the group consisting of
hydrogen,
alkyl of one to six carbon atoms,
hydroxy, and
alkoxy of one to six carbon atoms, or $R^4$ and $R^5$ taken together define a five-membered ring, with the proviso that $R^4$ and $R^5$ may not both be hydroxyl.

2. A compound as defined by claim 1, or a pharmaceutically acceptable salt thereof wherein M is —OH.

3. A compound as defined by claim 2, or a pharmaceutically acceptable salt thereof wherein A is alkylene of one to six carbon atoms.

4. A compound as defined by claim 3, or a pharmaceutically acceptable salt thereof wherein W Is selected from the group consisting of
pyridyl,
pyridyl substituted with
phenyl,
phenyl substituted with
halogen,
alkyl of one to six carbon atoms,
haloalkyl of one to six carbon atoms, or
alkoxy of one to six carbon atoms,
pyridyl, or
pyridyl substituted with
halogen,
alkyl of one to six carbon atoms, or
alkoxy of one to six carbon atoms.

5. A compound as defined by claim 3, or a pharmaceutically acceptable salt thereof wherein W is selected from the group consisting of:
quinolyl,
quinolyl substituted with
halogen,
alkyl of one to six carbon atoms,
phenyl,
phenyl substituted with
halogen,
alkyl of one to six carbon atoms,
haloalkyl of one to six carbon atoms, or
alkoxy of one to six carbon atoms,
pyridyl, or
pyridyl substituted with
halogen,
alkyl of one to six carbon atoms, or
alkoxy of one to six carbon atoms.

6. A compound as defined by claim 3, or a pharmaceutically acceptable salt thereof wherein W Is selected from the group consisting of:
quinolyl,
quinolyl substituted with
halogen,
alkyl of one to six carbon atoms
phenyl,
phenyl substituted with
halogen,
alkyl of one to six carbon atoms,
haloalkyl of one to six carbon atoms, or
alkoxy of one to six carbon atoms,
pyridyl, or
pyridyl substituted with
halogen,
alkyl of one to six carbon atoms, or
alkoxy of one to six carbon atoms.

7. A compound as defined by claim 3, or a pharmaceutically acceptable salt thereof wherein W is selected from the group consisting of
quinolyl, and
quinolyl substituted with
halogen,
alkyl of one to six carbon atoms,
phenyl,
phenyl substituted with
halogen,
alkyl of one to six carbon atoms,
haloalkyl of one to six carbon atoms, or
alkoxy of one to six carbon atoms,
pyridyl, or
pyridyl substituted with
halogen,
alkyl of one to six carbon atoms, or
alkoxy of one to six carbon atoms.

8. A compound or pharmaceutically acceptable salt thereof as defined by claim 7 wherein Y is phenylene.

9. A compound or pharmaceutically acceptable salt thereof as defined by claim 1 selected from the group consisting of:

bis(4-(2-quinolylmethoxy)phenyl)methyliminoxyacetic acid, 2-(bis(4-(2-quinolylmethoxy)phenyl)methylirninoxy) propionic acid, bis(4-(2-pyridylmethoxy)phenyl)methyliminoxyacetic acid, 2-(bis(4-(2-pyridylmethoxy)phenyl)methyliminoxy) propionic acid, bis(4-(6-fluoro-2-quinolylmethoxy)phenyl) methyliminoxyacetic acid, 2-(bis(4-(6-fluoro-2-quinolylmethoxy)phenyl) methyliminoxy)propionic acid, 4-(bis(4-(2-quinolylmethoxy)phenyl)methyliminoxy) pentanoic acid, 4-(bis(4-(2-quinolylmethoxyphenyl)methyliminoxy) pent-2-enoic acid, 3-(1,5-bis(4-(2-quinolylmethoxy)phenyl)pentyl) iminoxyacetic acid, 2-(3-(1,5-bis(4-(2-quinolylmethoxy)phenyl)pentyl) iminoxy) propionic acid, 2-(bis(4-(2-quinolylmethoxy)phenyl)methyliminoxy) propionic acid, and 4-(bis(4-(2-quinolylmethoxy)phenyl)methyliminoxy) pentanoic acid.

10. A compound or pharmaceutically acceptable salt thereof as defined by claim 1 selected from the group consisting of:

bis(4-(2-quinolylmethoxy)phenyl)methyliminoxyacetic acid, 2-(bis(4-(2-quinolylmethoxy)phenyl)methyliminoxy) propionic acid, 4-(bis(4-(2-quinolylmethoxy)phenyl)methyliminoxy) pentanoic acid, 2-(bis(4-(2-quinolylmethoxy)phenyl)methyliminoxy) propionic acid, sodium salt and 4-(bis(4-(2-quinolylmethoxy)phenyl)methyliminoxy) pentanoic acid, sodium salt.

11. A method for inhibiting lipoxygenase activity or leukotriene biosynthesis in a mammal in need of such treatment comprising administering to the mammal a therapeutically effective amount of a compound of claim 1.

12. A composition for inhibiting lipoxygenase activity or the biosynthesis of leukotrienes comprising a pharmaceutical carrier and a therapeutically effective amount of a compound of claim 1.

* * * * *

UNITED STATES PATENT AND TRADEMARK OFFICE
CERTIFICATE OF CORRECTION

PATENT NO. : 5,668,146
DATED : September 16, 1997
INVENTOR(S) : Brooks et al.

It is certified that error appears in the above-identified patent and that said Letters Patent is hereby corrected as shown below:

Column 29, line 6, change "NKR4R5" to --NR4R5--.

Column 30, line 35, change "methylirninoxy" to --methyliminoxy--.

Signed and Sealed this

Twenty-fourth Day of February, 1998

Attest:

BRUCE LEHMAN

Attesting Officer     Commissioner of Patents and Trademarks